United States Patent [19]

Sumita

[11] Patent Number: 5,180,426

[45] Date of Patent: Jan. 19, 1993

[54] COMPOSITION FOR FORMING CALCIUM PHOSPHATE TYPE SETTING MATERIAL AND PROCESS FOR PRODUCING SETTING MATERIAL

[75] Inventor: Masaya Sumita, Tokyo, Japan

[73] Assignee: Asahi Kogaku Kogyo K.K., Tokyo, Japan

[21] Appl. No.: 785,260

[22] Filed: Nov. 4, 1991

Related U.S. Application Data

[63] Continuation of Ser. No. 291,040, Dec. 28, 1988, abandoned, which is a continuation-in-part of Ser. No. 217,030, Jul. 11, 1988, abandoned.

[30] Foreign Application Priority Data

Dec. 28, 1987 [JP] Japan ................... 62-332904
Jun. 22, 1988 [JP] Japan ................... 63-153730

[51] Int. Cl.$^5$ .............................................. C09K 3/00
[52] U.S. Cl. .................................... 106/35; 501/1; 623/16; 433/228.1
[58] Field of Search ................. 106/35; 501/1; 623/16; 433/228.1

[56] References Cited

U.S. PATENT DOCUMENTS

| | | | |
|---|---|---|---|
| 4,093,576 | 6/1978 | de Wijn | 623/16 X |
| 4,191,747 | 3/1980 | Scheicher | 106/35 X |
| 4,264,493 | 4/1981 | Battista | 623/16 X |
| 4,394,373 | 7/1983 | Malette et al. | |
| 4,452,785 | 6/1984 | Malette et al. | |
| 4,497,075 | 2/1985 | Niwa et al. | 501/1 X |
| 4,518,430 | 5/1985 | Brown | 106/35 |
| 4,532,134 | 7/1985 | Malette et al. | |
| 4,548,959 | 10/1985 | Nagai et al. | 501/1 X |
| 4,605,623 | 8/1986 | Malette et al. | |

FOREIGN PATENT DOCUMENTS

| | | |
|---|---|---|
| 0147021 | 7/1985 | European Pat. Off. . |
| 59-171545 | 9/1984 | Japan . |
| 62-12705 | 1/1987 | Japan . |
| 63-143071 | 6/1988 | Japan . |
| 8601113 | 2/1986 | PCT Int'l Appl. . |

OTHER PUBLICATIONS

Monma et al, "Effect of Additives on Hydration and Hardening of Tricalcium Phosphate", Gypsum & Lime No. 188 (1984) pp. 11–15.
Malette et al., "Chitosan A New Hemostatic", the Annals of Thoracic Surgery, vol. 36, No. 1, Jul. 1983, pp. 55–58.
Akamatsu et al, "Hardening Material Consisted of Tricalcium Phosphate and Citric Acid", Seitai Zairyou (Biomaterial) vol. 5 (1) p. 21 (1987).
Sugihara et al, "Physical Properties for Hardening Material Composed of Tetracalcium Phosphate-Malic Acid-Citric Acid and Apatite Formation", Seitai Zairyon (Biomaterial) vol. 4(4) pp. 199–200 (1986).
Monroe, "Hydration Studies on $Ca_4P_2O_9$: A Potential Hard Tissue Cement", the Third World Biomaterials Congress, Apr. 21–25, 1988.
Page in Japanese language numbered "V-35" and Translation; Nagase et al., Niigata University Odontology Department Buccal surgery No. 1 Room.

Primary Examiner—Karl Group
Attorney, Agent, or Firm—Sughrue, Mion, Zinn, Macpeak & Seas

[57] ABSTRACT

A composition for forming a calcium phosphate type setting material comprising
(1) powder comprising at least one of α-tricalcium phosphate and tetracalcium phosphate; and
(2) a setting solution comprising an aqueous acidic solution having dissolved therein at least one polysaccharide selected from the group consisting of carboxymethyl chitin, glycol chitin, pullalan, high methoxypectin and chitosan in such an amount that the setting solution has a viscosity of 70 cp or more, and
a process for producing a calcium phosphate type setting material using such a composition.

29 Claims, 3 Drawing Sheets

FIG. 2

COMPOSITION FOR FORMING CALCIUM PHOSPHATE TYPE SETTING MATERIAL AND PROCESS FOR PRODUCING SETTING MATERIAL

This is a continuation of prior parent application Ser. No. 07/291,040 filed on Dec. 28, 1988, which is a continuation-in-part of prior parent application Ser. No. 07/217,030 filed Jul. 11, 1988 (now abandoned).

FIELD OF THE INVENTION

The present invention relates to a composition for forming calcium phosphate type setting material and a process for producing such a setting material. More particularly, the present invention relates to a composition for forming a calcium phosphate type setting material which is useful as a medical or dental cement material or a bone prosthesis. The present invention also relates to a process for producing a setting material in block form or other setting materials useful as artificial bones and dental roots.

BACKGROUND OF THE INVENTION

Calcium phosphate compounds, in particular hydroxyapatite, have an excellent biocompatibility and their use as biomaterials in medical or dental fields has been widely investigated.

Calcium phosphate compounds other than apatite are known to be converted to hydroxyapatite upon hydrolysis under certain conditions (such as acidic conditions) and set at the same time. In an attempt to exploit this phenomenon, several efforts have been made to use calcium phosphate powders as dental or medical cement materials (as described, for example, JP-A-63-12705, 62-161206, 59-182263 and 59-88351) (the term "JP-A" as used herein means an unexamined published Japanese patent application).

Calcium phosphate powders are set by mixing them with a setting solution. In order to ensure that° the setting material will do no harm to body tissues, it is desirable for the mixture to have a low pH and that the setting reaction will proceed in the neutral range. An aqueous solution of citric acid has heretofore been considered the best setting solution capable of satisfying these requirements. However, such an aqueous solution of citric acid still leaves room for improvement, especially when compared with acrylic cement materials which have been commonly used in the art. The considerable problem is that a mixture of a calcium phosphate powder and an aqueous citric acid solution is not gum-like and cannot be readily formed into a desired shape.

SUMMARY OF THE INVENTION

An object of the invention is to provide an improved composition for forming a calcium phosphate type setting material. This composition employs a powder component which can be produced by any suitable method; is highly gum-like; can be readily shaped into a desired form by kneading operations; allows a setting reaction to proceed uniformly and thoroughly in the neutral range; and produces a setting material which has high strength and yet does not harm body tissues.

Another object of the present invention is to provide a process for producing such a calcium phosphate type setting material.

Other objects and effects of the present invention will be apparent from the following description.

The present invention provides, in one aspect, a composition for forming a calcium phosphate type setting material comprising
  (1) powder comprising at least one of α-tricalcium phosphate and tetracalcium phosphate; and
  (2) a setting solution comprising an aqueous acidic solution having dissolved therein at least one polysaccharide selected from the group consisting of carboxymethyl chitin, glycol chitin, pullulan, high methoxy-pectin and chitosan in such an amount that the setting solution has a viscosity of 70 cp (centipoise) or more.

DETAILED DESCRIPTION OF THE INVENTION

As a result of various studies conducted in order to solve the aforementioned problems of the prior art, the present inventor has found that:

a composition for forming a calcium phosphate type setting material having good formability can be made from a powder component of calcium phosphate compound by using an aqueous acidic setting solution containing a polysaccharide in such an amount that the setting solution has a viscosity at room temperature of 70 cp (centipoise) or more, preferably from 100 to 20,000 cp, and more preferably from 500 to 10,000 cp;

a composition capable of being set mildly can be made by using an aqueous acidic setting solution containing at least one of a monosaccharide, an oligosaccharide, a sugaralcohol and a polyhydric alcohol;

setting materials of good quality can be produced from the above compositions; and a uniform mixture of α-tricalcium phosphate and tetracalcium phosphate can be prepared by calcining, at a temperature of from about 1,150° to 1,450° C. under reduced pressure, a calcium phosphate having a molar ratio of Ca/P of about 1.8 or less and more than 1.5.

The present invention has been accomplished on the basis of these findings.

In the present invention, powders comprising at least one of α-tricalcium phosphate and tetracalcium phosphate are used as a powder component of the composition. The powder component may further comprise at least one of β-calcium phosphate and hydroxyapatite. When these calcium phosphate powders are used as a mixture of two or more of them, the mixing ratio is not particularly limited, but the ratio of the total amount of α-tricalcium phosphate and tetracalcium phosphate to the total amount of the other components in the powder component is preferably ⅓ by weight or more in view of the activity on the setting reaction. These powder components need not be completely pure and they may contain minor amounts of impurities which are generated during the synthesis.

Among these powders, the following powders are preferably used in the present invention: (1) α-tricalcium phosphate, (2) tetracalcium phosphate, (3) a mixture of α-tricalcium phosphate and tetracalcium phosphate, (4) a mixture of α-tricalcium phosphate and hydroxyapatite, (5) a mixture of tetracalcium phosphate and hydroxyapatite, (6) a mixture of tetracalcium phosphate and β-tricalcium phosphate, and (7) a mixture of α-tricalcium phosphate and β-tricalcium phosphate.

The powder of α-tricalcium phosphate (1) can be prepared by: the dry method in which calcium carbonate and calcium pyrophosphate (which is obtained by heating calcium hydrogenphosphate dihydrate at 550° C. for 2 hours) are with each other at 1,200° C. for 1 hour (as described, e.g., in Gypsum & Lime, No. 188, page 11 (1984) and Seitai Zairyo (Journal of Japanese Society for Biomaterials), vol. 4, No. 3, page 51 (1986)); or the wet method in which phosphoric acid and calcium hydroxide are with each other in an aqueous solution followed by calcining at from 1,120° to 1,180° C. or higher temperatures (as described, e.g., in Bioceramics no Kaihatu to Rinsho (Bioceramics—Development and Clinical Application), page 86, published by Quintessnce Shuppan, Japan on Apr.10, 1987).

The powder of tetracalcium phosphate (2) can be prepared by the dry method in which calcium carbonate and calcium pyrophosphate are reacted with other at 1,500° C. (as described, e.g., in Shika Zairyo, Kikai (Journal of the Japanese Society for Dental Materials and Devices), vol. 5, special issue 7, page 50 (1986)).

The powder of a mixture of α-tricalcium phosphate and tetracalcium phosphate (3) can be prepared by: the thermal decomposition method in which calcium phosphate having a molar Ca/P ratio of more than 1.5 and 1.8 or less is calcined at from 1,150° to 1,450° C. under a reduced pressure, or in which hydroxyapatite obtained by the wet method is calcined at 1,500° C. for 24 hours (as described in Transaction of Showa-62 Annual Meeting of Ceramics Society of Japan, page 931 (May 12, 1987); or mixing α-tricalcium phosphate and tetracalcium phosphate each having been prepared separately (as described in Shika Zairyo, Kikai (Journal of the Japanese Society for Dental Materials and Devices), vol. 5, special issue 7, page 50 (1986)).

The powder of a mixture of α-tricalcium phosphate and hydroxyapatite (4) can be prepared by: the thermal decomposition method in which calcium phosphate having a molar Ca/P ratio of more than 1.5 and less than 1.67 is calcined at 1,000° C. or more, preferably from 1,150° to 1,450° C.; or mixing o tricalcium phosphate and hydroxyapatite each having been prepared separately (as described in JP-A-59-182263 and JP-A-59-88351).

The powder of hydroxyapatite can be prepared by: the dry method in which calcium carbonate and calcium pyrophosphate are reacted with each other in steam (as described, e.g., in Bioceramics no Kaihatu to Rinsho (Bioceramics—Development and Clinical Application), page 53, published by Quintessence Shuppan, Japan on Apr. 10, 1987); or the wet method in which phosphoric acid and calcium hydroxide are reacted each other in an aqueous solution (as described, e.g., in Bioceramics no Kaihatu to Rinsho (Bioceramics—Development and Clinical Application), page 53, published by Qintessence Shuppan, Japan on Apr. 10, 1987).

The powder of a mixture of tetracalcium phosphate and hydroxyapatite (5) can be prepared by mixing tetracalcium phosphate and hydroxyapatite each having been prepared separately.

The powder of a mixture of tetracalcium phosphate and β-tricalcium phosphate (6) can be prepared by mixing tetracalcium phosphate and β-tricalcium phosphate each having been prepared separately (as described in JP-A-59-182263).

The powder of β-tricalcium phosphate can be prepared by: the dry method in which calcium carbonate and calcium pyrophosphate are reacted with each other at 1,000° C. (as described, e.g., in J. Catal., vol 75, page 200 (1982)); or the wet method in which phosphoric acid and calcium hydroxide are reacted each other in an aqueous solution followed by calcining at 800° C (as described, e.g., in Bioceramics no Kaihatu to Rinsho (Bioceramics—Development and Clinical Application), page 86, published by Quintessnce Shuppan, Japan on Apr. 10, 1987).

The methods for preparing α-tricalcium phosphate and β-tricalcium phosphate are different from each other in the calcining temperature. The formation of α-tricalcium phosphate becomes predominant relative to the formation of β-tricalcium phosphate at a temperature range of from 1,120° to 1,180° C.

The powder of a mixture of α-tricalcium phosphate and β-tricalcium phosphate (7) can be prepared by: reacting phosphoric acid and calcium hydroxide followed by calcining at a temperature at which α-tricalcium phosphate and β-tricalcium phosphate are formed as a mixture; or mixing α-tricalcium phosphate and β-tricalcium phosphate each having been prepared separately.

The preparation of the powder of a mixture of α-tricalcium phosphate and tetracalcium phosphate (3) which is particularly preferably used in the present invention will be described in more detail below.

The two compounds, i.e., α-tricalcium phosphate and tetracalcium phosphate, may be synthesized separately and thereafter mixed in appropriate proportions.

Synthesis of α-tricalcium phosphate can be made by a known dry or wet process. Tetracalcium phosphate can be prepared by a known dry process involving the reaction between calcium pyrophosphate and calcium carbonate.

A mixture of α-tricalcium phosphate and tetracalcium phosphate can be prepared by the step of calcining, at a temperature of from about 1,150° C. to 1,450° C. under reduced pressure, a calcium phosphate having a molar ratio of Ca/P of about 1.8 or less and more than 1.5 so as to produce a mixture of α-tricalcium phosphate and tetracalcium phosphate.

In this method for producing the mixture using a reduced pressure, the calcium phosphate having a molar ratio of Ca/P of more than 1.5 but not exceeding about 1.8 can be readily synthesized by a wet method. If such calcium phosphate is calcined under reduced pressure at about 1,150° C. or more, it is thermally decomposed to form α-tricalcium phosphate and tetracalcium phosphate in admixture. The resulting mixture is uniform in composition. Such calcium phosphate generally starts to be thermally decomposed at a temperature near 1,400° C. if the pressure is atmospheric. In the method described above, because the pressure is subatmospheric, the reaction of thermal decomposition is allowed to proceed at a fairly high speed even at the relatively low temperature of about 1,150° C. This is beneficial to the purpose of simplifying the manufacturing steps and reducing the production cost. The low calcining temperature offers the additional advantage of providing a highly active powder for use as a powder component for calcium phosphate type setting materials.

The calcium phosphate used as the starting material in the method described above can be readily synthesized by a wet process in which an aqueous solution of phosphoric acid is reacted with a suspension of calcium hydroxide by a known method. The molar ratio of Ca/P of this calcium phosphate must be more than 1.5 and about 1.8 or less, preferably from about 1.6 to 1.8. If the molar ratio of Ca/P is 1.5, the product thus-obtained does not become a mixture but α-tricalcium phosphate per se. If the molar ratio of Ca/P exceeds about 1.8, calcium oxide which is deleterious to the human body will form during calcining. The Ca/P molar ratio of the calcium phosphate used as the starting material can be adjusted by changing the proportions of calcium hydroxide and phosphoric acid which are to be reacted in the synthesis process of the calcium phosphate. By changing the Ca/P molar ratio of the starting calcium phosphate, the proportions of α-tricalcium phosphate and tetracalcium phosphate to be finally produced can be adjusted to desired values.

After synthesis by a suitable method such as a wet process, the starting calcium phosphate is preferably rendered in powder form by suitable means such as filtration, centrifugation or spray-drying. It is also preferred for the calcium phosphate to be thoroughly dried to remove as much water as possibly by a suitable method such as precalcination at a temperature of about from 500° to 700° C. before it is thermally decomposed in a subsequent calcining step.

The thus prepared calcium phosphate is calcined under reduced pressure at a temperature of from about 1,150° C. to 1,450° C. If the calcining temperature is less than about 1,150° C., the intended thermal decomposition reaction will not take place to a practically acceptable extent even if the pressure is decreased.

The reason why the calcium phosphate is calcined under reduced pressure is that the calcining temperature can be lowered so as to simplify the manufacturing steps and to reduce the production costs, and that a product having a high activity can be attained The reduced pressure under which the calcium phosphate is calcined is preferably about 10 Pa or less, more preferably about $10^{-2}$ Pa or less.

When the mixture of α-tricalcium phosphate and tetracalcium phosphate is prepared by calcining, at a temperature of from about 1,150° C. to 1,450° C. under reduced pressure, a calcium phosphate having a molar ratio of Ca/P of about 1.8 or less and more than 1.5 can be obtained and because of the uniformity of the mixture, the activity on setting reaction of the mixture can be heightened and the setting reaction can proceed uniformly and sufficiently by which a setting material having a high strength can be obtained.

The preparation of the powder of a mixture of α-tricalcium phosphate and hydroxyapatite (4) which is particularly preferably used in the present invention is described in more detail below.

The two components, i.e., α-tricalcium phosphate and hydroxyapatite, may either be synthesized separately and thereafter mixed in appropriate proportions, or be produced simultaneously by calcining a specific calcium phosphate, i.e., the thermal decomposition method. In the present invention, it is preferred that these two components are produced simultaneously by thermal decomposition.

In the case where the two components are produced separately, each of them may be prepared by any known method such as a wet method and a dry method, and then mixed in appropriate proportions by any known method such as by using a mortar or a ball mill.

In the case where the two components are produced simultaneously, a mixture of α-tricalcium phosphate and hydroxyapatite used in the present invention is prepared by the step of calcining, at a temperature of about 1,000° C. or more, a calcium phosphate having a molar ratio of Ca/P of less than 1.67 and more than 1.5, preferably from 1.62 to 1.54.

The calcium phosphate used as a starting material for producing a mixture of α-tricalcium phosphate and hydroxyapatite can be prepared by reacting a phosphoric compound with a calcium compound in which the amount of the phosphoric compound is in excess of the stoichiometric amount required for produce hydroxyapatite. For example, in a known method for producing hydroxyapatite by reacting an aqueous solution of phosphoric acid and a dispersion of calcium hydroxide, an excess amount of phosphoric acid is used to obtain the objective calcium phosphate.

The molar ratio of Ca/P of the calcium phosphate must be less than 1.67 and more than 1.5 and preferably from 1.62 to 1.54. If it is 1.5, α-tricalcium phosphate per se, which is a component of the objective mixture, is produced. If it is 1.67, hydroxyapatite per se, which is a component of the objective mixture, is produced.

The molar ratio of Ca/P of the calcium phosphate can be controlled by changing the mixing ratio of calcium hydroxyide and phosphoric acid. The ratio of α-tricalcium phosphate and hydroxyapatite of the mixture can be controlled by changing the molar ratio of Ca/P of the calcium phosphate.

The calcium phosphate is preferably produced by synthesizing by a wet method and then powderized by filtering, centrifuging, spray-drying, etc.

The thus prepared calcium phosphate is calcined at a temperature of about 1,000° C. or more, preferably from about 1,150° C. to 1,450° C. If the calcining temperature is less than about 1,000° C., the intended thermal decomposition reaction will not take place to a practically acceptable extent, or only β-tricalcium phosphate is formed which has a relatively low activity on the setting reaction even if the decomposition reaction takes place. If the calcining temperature is too high, the activity on setting reaction of the mixture is reduced.

When the mixture of α-tricalcium phosphate and hydroxyapatite is prepared by calcining the calcium phosphate having a Ca/P molar ratio of more than 1.5 and less than 1.67, because of the uniformity of the mixture, the activity on setting reaction of the mixture can be heightened and the setting reaction can proceed uniformly and sufficiently by which a setting material having a high strength can be obtained.

In any of the above-described methods for producing calcium phosphate compounds, the wet methods can also be conducted according, e.g., to in *Ann. Chim. (Paris)*, vol. 7, 808 and 823 (1952); *J. Res. Nat. Bur. Stand.*, vol. 72A, 773 (1986); and *Archs. Oral Biol.*, vol. 23, 329 to 336 (1978); and the dry methods can be conducted according, e.g., to *Arch. Intern. Physiol. Biochim.*, vol. 72, 337 (1964); *Chem. Abstr.*, vol. 60, 15418a (1964); and *Studii Cercetari Chim.*, vol. 13, 157 (1962).

The mixture of α-tricalcium phosphate and hydroxyapatite prepared by the above thermal decomposition method and the mixture of α-tricalcium phosphate and tetracalcium phosphate prepared by the above thermal decomposition method can be preferably used as a powder component of the composition of the present invention and in the process for producing a setting material. Additionally, these mixtures may be used as a powder for thermal spray as described for example, in *Kinzoku Hyomen Gijutsu Binran* (Handbook of Metal Surface Treating Technology), pp. 1,132 to 1,139 (Nikkan Kogyo Shinbunsha, Japan, 1963) and JP-A-63-65871. If desired, the powder of these mixtures may be granulated, thereby producing a medical and dental granulated bone prosthesis. The granulated prosthesis has the advantage that it can be placed at will in any areas of any shape that need prosthetic treatments. Other applications of these mixtures include use as a column packing similar to the case of the hydroxyapatite.

The aqueous acidic solution for use as a setting solution in the present invention may contain various inorganic and organic acids dissolved therein. Examples thereof include inorganic acids such as phosphoric acid, and organic acids such as acetic acid, lactic acid, citric acid, malic acid, malonic acid, succinic acid, glutaric acid, tartaric acid and polyacrylic acid. In the present invention, these acids are used in aqueous solution having acid concentrations which are preferably about 25 wt % or more, more preferably from about 25 to 55 wt %. If the acid concentration of the aqueous acidic solution is less than about 25 wt %, the setting material obtained by mixing it with the powder component may not exhibit the desired strength.

Preferred examples of the aqueous acidic solution include a citric acid solution having an acid concentration of about 40 wt %, a malic acid solution having an acid concentration of about 40 wt %, a phosphoric acid solution having an acid concentration of about 40 wt %, and a polyacrylic acid solution having an acid concentration of about 25 wt %.

In accordance with one aspect of the present invention, a polysaccharide is added and dissolved in the various aqueous acidic solutions described above to form a setting solution. The polysaccharides preferably will not harm living tissues and have affinity for living tissues. Examples thereof include carboxymethyl chitin, glycol chitin, pullulan, high methoxy-pectin and chitosan with chitosan being particularly preferred. The term "chitosan" as used herein means a partially or completely deacetylated chitin. The deacetylation degree of chitosan and the substitution degree of carboxymethyl chitin and glycol chitin are not particularly limited.

The polysaccharides are dissolved in the aqueous acidic solutions in such an amount that the resulting setting solution has a viscosity at room temperature measured by a rotation viscometer of 70 cp or more, preferably from 100 to 20,000 cp, and more preferably from 500 to 10,000 cp.

By using the polysaccharide-containing aqueous acidic solutions as setting solutions, the powder component can be set mildly in the neutral range, and the composition for forming setting materials is gum-like enough to be readily formed into any complex shape.

The setting reaction can be allowed to proceed even more mildly by further adding and dissolving at least one of a monosaccharide, an oligosaccharide, a sugaralcohol and a polyhydric alcohol in the polysaccharide-containing setting solution.

Examples of the monosaccharide include glucose and fructose, which may be used either alone or in admixture. Examples of the oligosaccharide include saccharose, maltose, lactose and raffinose, which may be used either alone or in admixture. Examples of the sugaralcohol include sorbitol, mannitol and xylitol, which may also be used either alone or in combination. Examples of the polyhydric alcohol include glycols (such as ethylene glycol) and glycerine which may also be used either alone or in combination. Monosaccharides, oligasaccharides, sugaralcohols and polyhydric alcohol, may be used either independently or in combination.

When at least one of monosaccharides, oligosaccharides, sugaralcohols and polyhydric alcohols are used, the setting reaction can proceed mildly and sufficiently even if the powder component having a high activity, e.g., a mixture of $\alpha$-tricalcium phosphate and tetracalcium phosphate, and a mixture of $\alpha$-tricalcium phosphate and hydroxyapatite which are prepared by the thermal decomposition, is used.

The total concentration of monosaccharides, oligosaccharides, sugaralcohols and polyhydric alcohols in the setting solution is preferably from about 5 to 40 wt %, more preferably from about 10 to 30 wt %. If the concentration of these additives exceeds about 40 wt %, increased difficulty will be encountered in dissolving them in the setting solution.

In any case, the powder component and the setting solution are preferably mixed in such proportions that the ratio of the powder to the solution is within the range of from about 0.4 to 2.7 by weight, more preferably from about 0.4 to 2.0 by weight. If the ratio of the powder to the solution is less than about 0.4, the solids content is too low to ensure desired strength for the setting material. If the ratio of the powder to the solution exceeds about 2.7, it becomes difficult to attain uniform mixing of the powder and the solution.

The setting material thus obtained by using the composition according to the present invention may further be calcined to improve the mechanical strength.

If a foaming agent (e.g., hydrogen peroxide) or a substance which disappears by calcining (e.g., polystyrene beads) is added to the material before completely setting, porous material can be obtained by calcining.

The following examples are provided for the purpose of further illustration the present invention but are in no way to be taken as limiting. All parts, ratio and presents are by weight unless otherwise indicate.

EXAMPLE 1

Figure 1:
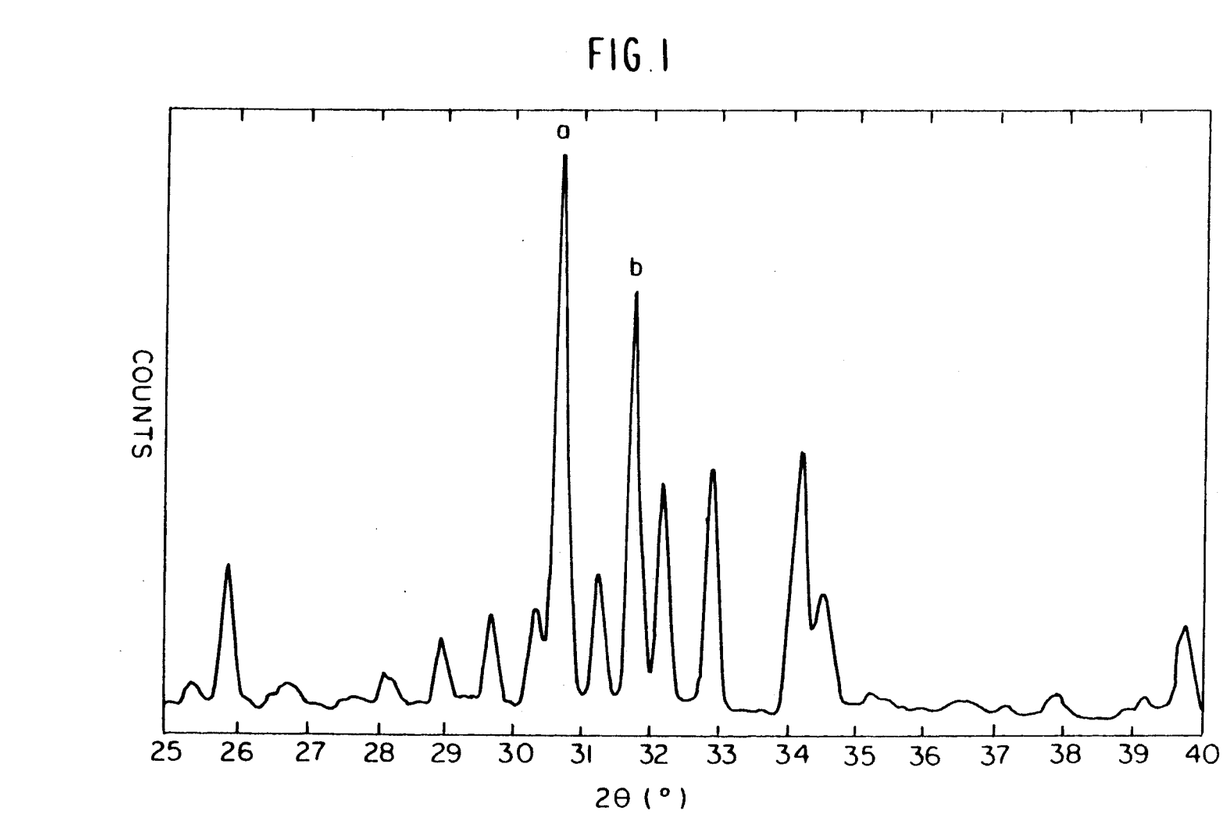
FIG. 1 is a X-ray diffraction scan of the mixture of α-tricalcium phosphate and hydroxyapatite prepared in Example 1.

A calcium phosphate having a molar ratio of Ca/P of 1.57 was obtained by reacting an aqueous solution of phosphoric acid and a dispersion of calcium hydroxide in a conventional method followed by drying. The thus-obtained calcium phosphate was calcined at 1,200° C. for 1 hour. The result of X-ray diffractiometry of the product obtained is shown in FIG. 1. In FIG. 1, peak a for $\alpha$-tricalcium phosphate and peak b for hydroxyapatite appeared which confirm that an mixture of $\alpha$-tricalcium phosphate and hydroxyapatite was formed by thermal decomposition of the calcium phosphate.

1 g of the mixture of $\alpha$-tricalcium phosphate and hydroxyapatite obtained above was mixed with 1 g of a setting solution prepared by dissolving 3 g of saccharose in 10 g of a 40% aqueous solution of citric acid to prepare a setting composition. The composition was set in about 10 minutes to produce a setting material having a high strength.

EXAMPLE 2

1 g of the mixture of $\alpha$-tricalcium phosphate and hydroxyapatite obtained in Example 1 was mixed with 1 g of a setting solution composed of an aqueous solution of polyacrylic acid containing 1% of saccharose (acid concentration: about 25%, produced by Wako Pure Chemical Co., Ltd.) to prepare a setting composition. The composition was set in about 15 minutes to produce a setting material having a high strength.

EXAMPLE 3

1 g of the mixture of α-tricalcium phosphate and hydroxyapatite obtained in Example 1 was mixed with 1 g of a setting solution composed of a 40% aqueous solution of phosphoric acid containing 10% of saccharose to prepare a setting composition. The composition was set in about 30 seconds to produce a setting material having a high strength.

COMPARATIVE EXAMPLE 1

1 g of the mixture of α-tricalcium phosphate and hydroxyapatite obtained in Example 1 was mixed with 1 g of a setting solution composed of a 40% aqueous solution of phosphoric acid. The mixture immediately reacted vigorously with a great amount of exothermic heat, and once produced a setting material, but the material was broken immediately.

EXAMPLES 4 TO 16

1 g of the mixture of α-tricalcium phosphate and hydroxyapatite obtained in Example 1 was mixed with 1 g of a setting solution shown in Table 1 below to prepare a setting composition.

TABLE 1

| | Setting solution | | |
|---|---|---|---|
| Example | Aqueous acidic solution | Additive | Setting time (min) |
| 4 | 40% citric acid | 25% glucose | 10 |
| 5 | 40% citric acid | 25% sorbitol | 10 |
| 6 | 40% citric acid | 25% glycerin | 12 |
| 7 | 40% citric acid | 0.5% chitosan* | 1 |
| 8 | 40% malic acid | 25% glycerin | 14 |
| 9 | 40% malic acid | 25% saccharose | 15 |
| 10 | 40% phosphoric acid | 30% glycerin | 1 |
| 11 | 40% phosphoric acid | 0.5% chitosan* | 0.2 |
| 12 | 25% polyacrylic acid | 5% glucose | 15 |
| 13 | 25% polyacrylic acid | 5% sorbitol | 15 |
| 14 | 40% citric acid | 25% saccharose + 0.5% chitosan* | 15 |
| 15 | 40% phosphoric acid | 25% saccharose + 0.5% chitosan* | 1 |
| 16 | 40% malic acid | 25% glycerin + 0.5% chitosan* | 17 |

Note: *Chitosan was a commercial product, "Flonac N" made by Kyowa Yushi Kogyo K. K.

In Example 7, the viscosity at room temperature of the setting solution was 1,000 cp.

The composition was set in the period of time shown in Table 1 to produce a setting material having a high strength. In the case where the setting solution contained chitosan as a polysaccharide, the mixture of the powder and the setting solution provided a plastic gum-like composition which was easily shaped into a desired form.

EXAMPLE 17

Figure 2:
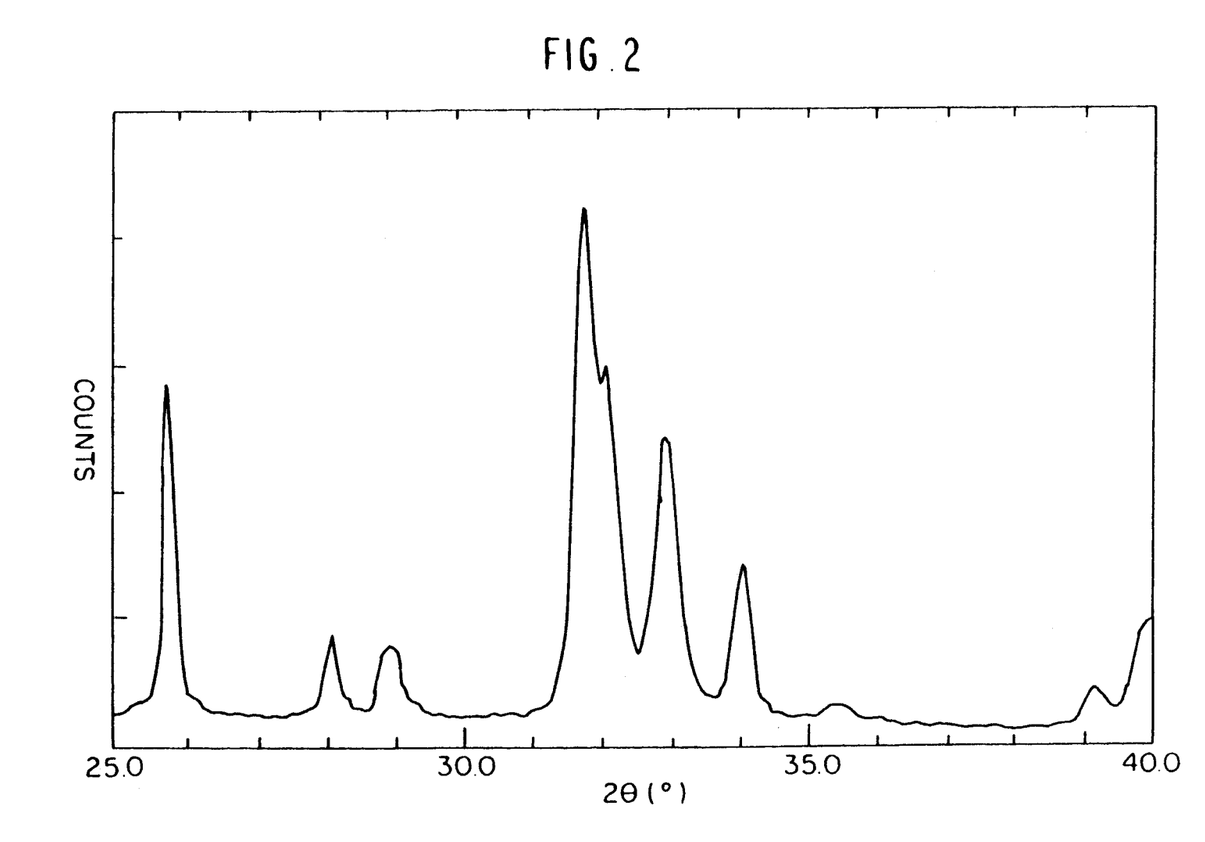
FIG. 2 is a X-ray diffraction scan of the calcium phosphate synthesized in Example 17.

An aqueous solution of phosphoric acid was reacted with a suspension of calcium hydroxide by a conventional method, and the reaction product was dried to obtain calcium phosphate. The identity of the product was established by X-ray diffraction, the results of which are shown by an X-ray diffraction scan in FIG. 2. A chemical analysis revealed that the resulting calcium phosphate had a Ca/P molar ratio of 1.67.

Figure 3:
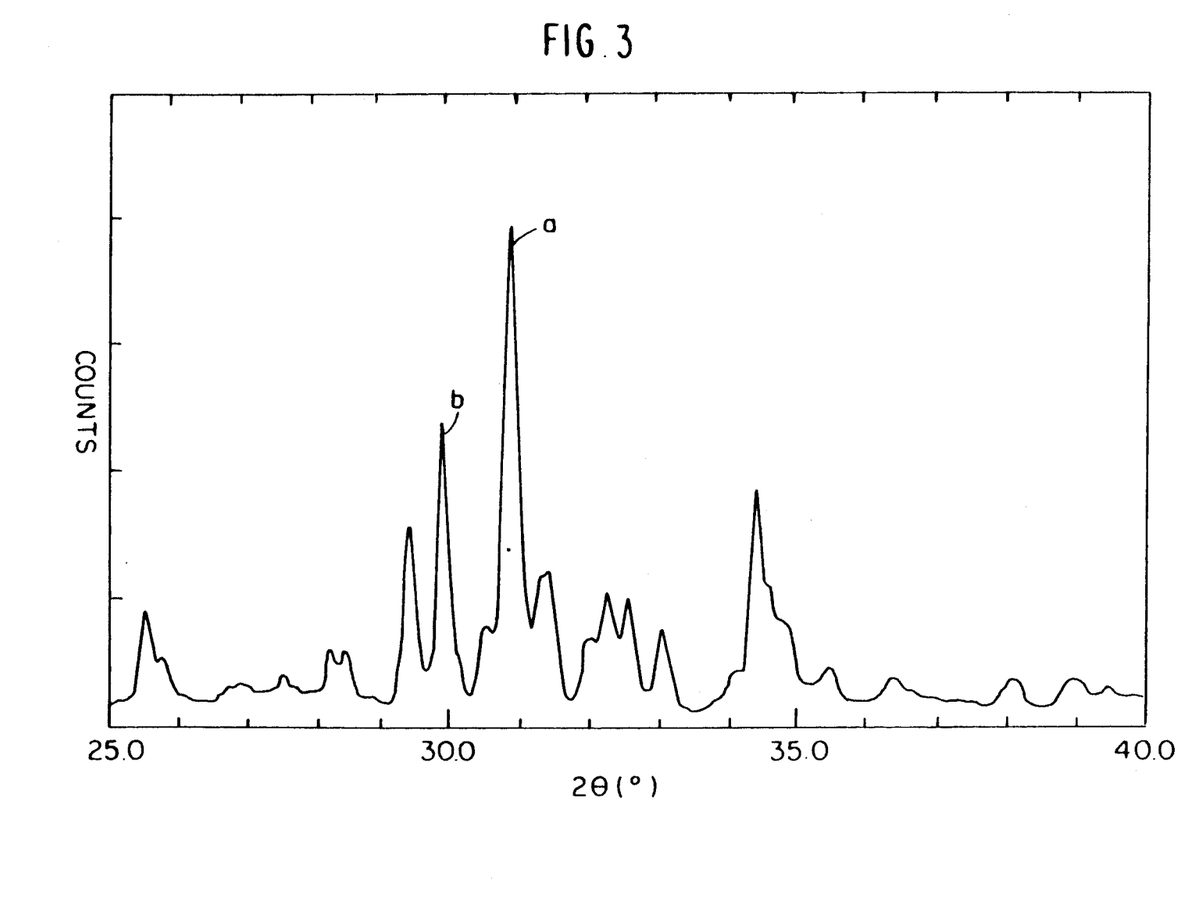
FIG. 3 is a X-ray diffraction scan of the powder prepared in Example 17 in accordance with the present invention.

This calcium phosphate was calcined at 1,200° C. for 1 hour at a pressure of $1.3 \times 10^{-4}$ Pa. The resulting product was analyzed by X-ray diffraction as above and the results are shown in FIG. 3. The appearance of two characteristic peaks a (α-tricalcium phosphate) and b (tetracalcium phosphate) verified the production of a mixture of α-tricalcium phosphate and tetracalcium phosphate by thermal decomposition of the calcium phosphate.

2 g of the above-obtained powder mixture of α-tricalcium phosphate and tetracalcium phosphate was mixed with 1 g of a setting solution having a viscosity at room temperature of 200 cp which was prepared by adding 3 g of glucose and 0.2 g of carboxymethyl chitin (CM-Chitin 100 made by Katokichi Co., Ltd.) to 10 g of a 45% aqueous solution of malic acid. The resulting plastic composition was highly gum-like and set in about 12 minutes to produce a setting material having a high strength.

EXAMPLE 18

The same procedures as in Example 17 were repeated except that 0.2 g of glycol chitin (made by Katokichi Co., Ltd.) was used instead of the carboxymethyl chitin used in Example 17. The resulting plastic composition was highly gum-like and set in about 12 minutes to produce a setting material having a high strength.

EXAMPLE 19

The same procedures as in Example 17 were repeated except that 0.2 g of high methoxy-pectin (Rapid Set Baking 150SAG made by Mero Rousselot Satia) was used instead of the carboxymethyl chitin used in Example 17. The viscosity at room temperature of the setting solution was 900 cp. The resulting plastic composition was highly gum-like and set in about 15 minutes to produce a setting material having a high strength.

EXAMPLE 20

The same procedures as in Example 17 were repeated except that 10 g of pullulan (PF20 made by Hayashibara Co., Ltd.) was used instead of the carboxymethyl chitin used in Example 17. The resulting plastic composition was highly gum-like and set in about 20 minutes to produce a setting material having a high strength.

COMPARATIVE EXAMPLE 2

The same procedures as in Example 17 were repeated except that 0.2 g of methylcellulose (made by Wako Pure Chemical Co., Ltd.) was used instead of the carboxymethyl chitin used in Example 17. The resulting composition was not gum-like but set in about 12 minutes to produce a setting material having a high strength.

EXAMPLE 21

As aqueous solution of phosphoric acid was reacted with a suspension of calcium hydroxide by a conventional method. The reaction product was dried and calcined at 1,200° C. to obtain α-tricalcium phosphate in powder form. 2 grams of this powder was mixed with 1 g of a setting solution having a viscosity at room temperature of 6,000 cp prepared by dissolving 0.1 g of chitosan ("Flonac N" made by Kyowa Yushi Kogyo K.K.) in 10 g of an aqueous solution of 40% citric acid. A plastic gum-like composition was obtained and this composition set in about 7 minutes to produce a setting material having a high strength.

EXAMPLE 22

An aqueous solution of phosphoric acid was reacted with a suspension of calcium hydroxide by a conventional method. The reaction product was dried and calcined at 1,200° C. to obtain α-tricalcium phosphate in powder form. 2 grams of this powder was mixed with 1 g of a setting solution prepared by dissolving 0.1 g of chitosan ("Flonac N" made by Kyowa Yushi Kogyo K.K.) and 3 g of saccharose in 10 g of an aqueous solution of 40% citric acid. A plastic gum-like composition was obtained and this composition set in about 10 minutes to produce a setting material having a high strength.

EXAMPLE 23

Calcium pyrophosphate was reacted with calcium carbonate by a conventional method, and calcined to obtain tetracalcium phosphate in powder form. 2 grams of this powder was mixed with 1 g of a setting solution prepared by dissolving 0.1 g of chitosan ("Flonac N" made by Kyowa Yushi Kogyo K.K.) and 3 g of saccharose in 10 g of an aqueous solution of 40% citric acid. A plastic gum-like composition was obtained and this composition set in about 5 minutes to produce a setting material having a high strength.

EXAMPLE 24

α-Tricalcium phosphate and tetracalcium phosphate were prepared separately by conventional methods and mixed at a weight ratio of 2/1 to make a mixed powder. 2 grams of this mixed powder was mixed with 1 g of a setting solution prepared by dissolving 0.1 g of chitosan ("Flonac N" made by Kyowa Yushi Kogyo K.K.) in 10 g of an aqueous solution of 40% citric acid. A plastic gum-like composition was obtained and this composition set in about 5 minutes to produce a setting material having a high strength.

EXAMPLE 25

2 grams of the mixed powder prepared in Example 24 was mixed with 1 g of a setting solution prepared by dissolving 0.1 g of chitosan ("Flonac N" made by Kyowa Yushi Kogyo K.K.) and 3 g of saccharose in 10 g of an aqueous solution of 40% citric acid. A plastic gum-like composition was obtained and this composition set in about 7 minutes to produce a setting material having a high strength.

EXAMPLE 26 TO 37

2 grams of a powder indicated in Table 2 was mixed with 1 g of a setting solution indicated in Table 2 (Chitosan was "Flonac N" made by Kyowa Yushi Kogyo K.K.). Similar to the cases of Examples 21 to 25, plastic gum-like compositions were obtained and setting materials having a high strength could be produced from the compositions. The periods of time required for these compositions to set are also shown in Table 2, in which α-TCP and COP denote α-tricalcium phosphate and tetracalcium phosphate, respectively.

TABLE 2

| | | Composition of setting solution | | | | | | Time to set (min) |
|---|---|---|---|---|---|---|---|---|
| | | Aqueous acidic solution | | Polysaccharide | | Other additives | | |
| Example | Powder composition | acid and its concentration | amount (g) | | amount (g) | | amount (g) | |
| 26 | α-TCP | 40% citric acid | 10 | chitosan | 0.1 | glycerin | 3 | 10 |
| 27 | COP | 40% citric acid | 10 | chitosan | 0.1 | sorbitol | 3 | 5 |
| 28 | 2:1 mixture of α-TCP + COP | 40% citric acid | 10 | chitosan | 0.1 | glucose | 3 | 7 |
| 29 | α-TCP | 40% malic acid | 10 | chitosan | 0.1 | — | — | 7 |
| 30 | α-TCP | 40% malic acid | 10 | chitosan | 0.1 | glucose | 3 | 10 |
| 31 | COP | 40% malic acid | 10 | chitosan | 0.1 | glycerin | 3 | 5 |
| 32 | 2:1 mixture of α-TCP + COP | 40% malic acid | 10 | chitosan | 0.1 | sorbitol | 3 | 7 |
| 33 | COP | 40% malic acid | 10 | chitosan | 0.1 | saccharose | 3 | 5 |
| 34 | α-TCP | 40% phosphoric acid | 10 | chitosan | 0.1 | saccharose + glycerin | 3 + 3 | 2 |
| 35 | COP | 25% polyacrylic acid | 10 | chitosan | 0.1 | — | — | 10 |
| 36 | α-TCP | 25% polyacrylic acid | 10 | chitosan | 0.1 | glycerin | 3 | 20 |
| 37 | 2:1 mixture of α-TCP + COP | 25% polyacrylic acid | 10 | chitosan | 0.1 | saccharose | 3 | 15 |

COMPARATIVE EXAMPLE 3

The same procedures as in Example 21 were repeated except that chitosan was not added to the setting solution. The composition obtained was not gum-like and had a deteriorated formability although the composition hardened in about 2 minutes.

EXAMPLE 38

3 grams of the powder mixture of α-tricalcium phosphate and tetracalcium phosphate obtained in Example 17 was mixed with 2 g of a commercial aqueous solution of gluconic acid (made by Wako Pure Chemical Industries, Ltd.; concentration, ca. 50%). The mixture underwent a hydrolytic reaction and set in about 1 hour.

EXAMPLE 39

The powder prepared as in Example 38 was mixed with setting solutions (indicated in Table 3) at a weight ratio of 1/1 and setting materials were obtained. The setting times and the temperatures produced by the exothermic reaction of the setting process are also shown in Table 3.

TABLE 3

| Composition of setting solution (wt %) | | | | Setting time (min) | Temperature (°C.) |
|---|---|---|---|---|---|
| Citric acid | Glycerin | Sorbitol | Saccharose | | |
| 45 | 10 | 0 | 0 | 0.75 | 55 |
| 45 | 20 | 0 | 0 | 2 | 51 |
| 45 | 30 | 0 | 0 | 8 | 45 |
| 45 | 0 | 10 | 0 | 0.8 | 53 |
| 45 | 0 | 20 | 0 | 2 | 51 |
| 45 | 0 | 0 | 10 | 1 | 52 |
| 45 | 0 | 0 | 20 | 2.8 | 49 |
| 45 | 0 | 0 | 0 | 0.5 | 66 |

EXAMPLE 40

The mixture of α-triacalcium phosphate and tetracalcium phosphate prepared in Example 38 was used as a powder component. 2 grams of this powder was mixed with 1 g of a setting solution prepared by dissolving 0.1 g of chitosan ("Flonac N" made by Kyowa Yushi Kogyo K.K.) in 10 g of an aqueous solution of 40% citric acid. A plastic gum-like composition was obtained and this composition set in about 2 minutes to produce a setting material having a high strength.

COMPARATIVE EXAMPLE 4

The same procedures as in Example 40 were repeated except that chitosan was not added to the setting solution. The composition obtained was not gum-like and had a deteriorated formability although the composition set in about 2 minutes.

EXAMPLE 41

The mixture of α-tricalcium phosphate and tetracalcium phosphate prepared in Example 38 was used as a powder component. 2 grams of this powder was mixed with 1 g of a setting solution prepared by dissolving 3 g of saccharose and 0.1 g of chitosan ("Flonac N" made by Kyowa Yushi Kogyo K.K.) in 10 g of an aqueous solution of 40% citric acid. A plastic gum-like composition was obtained and this composition set in about 9 minutes to produce a setting material having a high strength.

COMPARATIVE EXAMPLE 5

The same procedures as in Example 41 were repeated except that chitosan was not added to the setting solution. The composition obtained was not gum-like and had a deteriorated formability although the composition set in about 2 minutes.

COMPARATIVE EXAMPLE 6

The same procedures as in Example 17 were repeated except that chitosan (Kimitsu Chitosan F made by Kimitsu Chemicals Co., Ltd.) was used instead of carboxymethyl chitin used in Example 17 so as to prepare a setting solution having a viscosity at room temperature of 50 cp. The composition obtained was not gum-like.

In accordance with one aspect of the present invention, a calcium phosphate compound is used as a powder component and mixed with a setting solution which is an aqueous acidic solution having a polysaccharide dissolved therein. The resulting composition is highly gum-like and can be readily formed into a desired shape before setting. The setting reaction which occurs is mild and it proceeds at a moderate rate and uniformly to produce a setting material having a high strength and which yet will not harm body tissues.

A mixture of α-tricalcium phosphate and tetracalcium phosphate can be readily prepared by calcining a calcium phosphate with a molar ratio of Ca/P of more than 1.5 and about 1.8 or less at a temperature of about from 1,150° C. to 1,450° C. under reduced pressure. In this preferred embodiment, an aqueous acidic solution containing not only a polysaccharide but also at least one of glycerin, a monosaccharide, an oligosaccharide and a sugaralcohol may preferably be used as a setting solution. This offers further advantage of allowing the setting reaction to proceed more uniformly to a fuller extent at a moderate and mild rate, thereby producing a setting material having a high strength and which yet will not harm body tissues.

Therefore, the present invention provides a composition which is useful as a medical or dental cement material or a bone prosthetic material and which, immediately before use, is rendered sufficiently gum-like by mixing the powder and the setting solution to replace defects of a bone or tooth, and is subsequently set. In addition, the present invention provides a setting biomaterial of a desired shape such as a setting material in block form, an artificial bone or dental root.

While the invention has been described in detail and with reference to specific examples thereof, it will be apparent to one skilled in the art that various changes and modifications can be made therein without departing from the spirit and scope thereof.

What is claimed is:

1. A composition for forming a calcium phosphate setting material comprising
   (1) powder comprising at least one of α-tricalcium phosphate and tetracalcium phosphate; and
   (2) a setting solution comprising an aqueous acidic solution having dissolved therein at least one polysaccharide selected from the group consisting of carboxymethyl chitin, glycol chitin, pullulan, high methoxy-pectin and chitosan in such an amount that said setting solution has a viscosity at room temperature of 70 cp or more.

2. A composition as claimed in claim 1, wherein the acid concentration of said acidic aqueous solution is about 25 wt % or more.

3. A composition as claimed in claim 2, wherein the acid concentration of said acidic aqueous solution is from about 25 to 55 wt %.

4. A composition as claimed in claim 1, wherein said acidic aqueous solution is an aqueous solution of an organic acid.

5. A composition as claimed in claim 4, wherein said acidic aqueous solution is an aqueous solution of an organic acid selected from the group consisting of acetic acid, lactic acid, citric acid, malic acid, malonic acid, succinic acid, glutaric acid, tartaric acid, and polyacrylic acid.

6. A composition as claimed in claim 5, wherein said acidic aqueous solution is selected from the group consisting of a citric acid solution having an acid concentration of about 40 wt %, a malic acid solution having an acid concentration of about 40 wt %, and a polyacrylic acid solution having an acid concentration of about 25 wt %.

7. A composition as claimed in claim 1, wherein said acidic aqueous solution is an aqueous solution of an inorganic acid.

8. A composition as claimed in claim 7, wherein said acidic aqueous solution is an aqueous solution of phosphoric acid.

9. A composition as claimed in claim 8, wherein said acidic aqueous solution is a phosphoric acid solution having an acid concentration of about 40 wt %.

10. A composition as claimed in claim 1, wherein said setting solution has a viscosity of from 100 to 20,000 cp.

11. A composition as claimed in claim 10, wherein said setting solution has a viscosity of from 500 to 10,000 cp.

12. A composition as claimed in claim 1, wherein said polysaccharide is chitosan.

13. A composition as claimed in claim 1, wherein the ratio of said powder to said setting solution is from about 0.4 to 2.7 by weight.

14. A composition as claimed in claim 13, wherein the ratio of said powder to said setting solution is from about 0.4 to 2.0 by weight.

15. A composition as claimed in claim 1, wherein ratio of the total amount of α-tricalcium phosphate and tetracalcium phosphate to the total amount of the other components in said powder is ½ by weight or more.

16. A composition as claimed in claim 1, wherein said powder further comprises at least one of β-tricalcium phosphate and hydroxyapatite.

17. A composition as claimed in claim 1, wherein said powder is selected from the group consisting of α-tricalcium phosphate, tetracalcium phosphate, a mixture of α-tricalcium phosphate and tetracalcium phosphate, a mixture of α-tricalcium phosphate and hydroxyapatite, a mixture of tetracalcium phosphate and hydroxyapatite, a mixture of tetracalcium phosphate and β-tricalcium phosphate, and a mixture of α-tricalcium phosphate and β-tricalcium phosphate.

18. A composition as claimed in claim 17, wherein said powder is a mixture of α-tricalcium phosphate and tetracalcium phosphate.

19. A composition as claimed in claim 18, wherein said powder is produced by the step of calcining, at a temperature of from about 1,150° C. to 1,450° C. under reduced pressure, a calcium phosphate having a molar ratio of Ca/P of about 1.8 or less and more than 1.5.

20. A composition as claimed in claim 19, wherein said calcium phosphate has a molar ratio of Ca/P of from about 1.6 to 1.8.

21. A composition as claimed in claim 19, wherein said calcium phosphate is calcined under a pressure of about 10 Pa or less.

22. A composition as claimed in claim 21, wherein said calcium phosphate is calcined under a pressure of about $10^{-2}$ Pa or less.

23. A composition as claimed in claim 17, wherein said powder is a mixture of α-tricalcium phosphate and hydroxyapatite.

24. A composition as claimed in claim 23, wherein said powder is produced by the step of calcining, at a temperature of about 1,000° C. or more, a calcium phosphate having a molar ratio of Ca/P of less than 1.67 and more than 1.5.

25. A composition as claimed in claim 24, wherein said powder is produced by the step of calcining, at a temperature of from about 1,150° to 1,450° C. or more, a calcium phosphate having a molar ratio of Ca/P of from 1.62 to 1.54.

26. A composition as claimed in claim 1, wherein said setting solution further comprises at least one member selected from the group consisting of a monosaccharide, and oligosaccharide, a sugaralcohol and a polyhydric alcohol.

27. A composition as claimed in claim 26, wherein the concentration of said at least one member selected from the group consisting of a monosaccharide, an oligosaccharide, a sugaralcohol and a polyhydric alcohol in said setting solution is from about 5 to 40 wt %.

28. A composition as claimed in claim 27, wherein the concentration of said at least one member selected from the group consisting of a monosaccharide, an oligosaccharide, a sugaralcohol and a polyhydric alcohol in said setting solution is from 10 to 30 wt %.

29. A process for producing a calcium phosphate setting material comprising the step of mixing
  (1) powder comprising at least one of α-tricalcium phosphate and tetracalcium phosphate; and
  (2) a setting solution comprising an aqueous acidic solution having dissolved therein at least one polysaccharide selected from the group consisting of carboxymethyl chitin, glycol chitin, pullulan, high methoxy-pectin and chitosan in such an amount that said setting solution has a viscosity of 70 cp or more, to form a setting material.

* * * * *